United States Patent [19]

Mugica

[11] Patent Number: 5,120,713
[45] Date of Patent: Jun. 9, 1992

[54] TREATMENT OF OBESITY WITH AN ALPHA-2-ADRENERGIC AGONIST AND A GROWTH HORMONE RELEASING PEPTIDE

[75] Inventor: Jesus D. Mugica, La Coruña, Spain

[73] Assignee: Applied Research Systems ARS Holding N.V., Curacao, Netherlands Antilles

[21] Appl. No.: 580,686

[22] Filed: Sep. 10, 1990

[51] Int. Cl.$^5$ .............................................. A61K 37/00
[52] U.S. Cl. ....................................... 514/17; 514/12; 514/16; 514/401
[58] Field of Search ...................... 514/12, 16, 17, 401

[56] References Cited

U.S. PATENT DOCUMENTS

| 4,224,316 | 9/1980 | Momany | 530/330 |
| 4,910,214 | 3/1990 | Karjalainen et al. | 514/396 |
| 4,910,215 | 3/1990 | Muller | 514/401 |

OTHER PUBLICATIONS

Williams, N. Engl. J. Med. 311:1403, 1984.
Kopelman, Clin. Endocrinol. 23:87, 1985.
Kopelman, Clin. Endocrinol. 24:157, 1986.
Loche, Clin. Endocrinol. 27:145, 1987.
Cordido, J. Clin. Endocrinol. Metab., 68:290, 1989.
Ghigo, J. Endocrinol Invest. 12:99, 1989.
Davis, J. Clin. Endocrinol. Metab. 65:1248, 1987.
Chatterjee, J. Endocrinol. 116:R1-R2, 1988.
Reiter, J. Pediat. Endocrinol. 3:21, 1988.
Arce, Neuroendocrinology 52/S1/90:119, 1990, Poster 3.50 of 2nd Int'l Cong. of Neuroendocrinology held Jun. 24–29, 1990.
Ghigo, "Effects of the Enhancement of the Cholinergic Activity on Growth Hormone Secretion in Children: Clinical Implications", Recent Advances in Basic and Clinical Neuroendocrinology (eds. Casanueva and Dieguez), pp. 241–251, 1989, Excerpta Medica, Amsterdam.
Cordido et al., Chem. Abstracts 113:453 (Jul. 1990), abstract 21676S.

*Primary Examiner*—Merrell C. Cashion, Jr.
*Assistant Examiner*—Choon Koh
*Attorney, Agent, or Firm*—Stephan P. Williams

[57] ABSTRACT

Obese patients may be effectively treated by cojointly administering an alpha-2-adrenergic agonist, such as clonidine, and a growth hormone releasing peptide, such as GHRH, to restore or substantially enhance growth hormone release in such patients.

17 Claims, No Drawings

TREATMENT OF OBESITY WITH AN ALPHA-2-ADRENERGIC AGONIST AND A GROWTH HORMONE RELEASING PEPTIDE

BACKGROUND OF THE INVENTION

This invention relates to the treatment of obesity with an alpha-2-adrenergic agonist and a growth hormone releasing peptide to induce growth hormone secretion in a patient with this condition.

It is generally known that obese patients have impaired growth hormone (GH) release, both in basal conditions and in response to a number of stimuli, including growth hormone releasing hormone (GHRH, also identified as GRF) (1,2,3,4). This has been postulated to be the result of a hypothalamic disorder (3), leading to a chronic state of somatostatin hypersecretion (5).

It is also known that administering to a normal patient an agent that interferes with the hypothalamic release of somatostatin will enhance growth hormone release. This effect has been shown for clonidine, an alpha-2-adrenergic agonist, and pyridostigmine, a cholinergic agonist, although the mechanism of action is different for each drug (6). Likewise, galanin has been shown to potentiate GHRH induced GH secretion in normal subjects (7) via the cholinergic pathways (8). It has also been recently shown that treatment of obese patients with the cholinergic agonist pyridostigmine will moderately restore the growth hormone responsiveness to GHRH administration, although to a substantially lesser degree than in normal subjects (5,11). While it has been shown that treatment of normal children and adults with clonidine and GHRH has resulted in significantly enhanced growth hormone levels (9,10), it was not known whether such treatment could be extended to obese patients given the lack of response by such patients to most other known treatments.

SUMMARY OF THE INVENTION

It has now been discovered that obese patients may be effectively treated by cojointly administering an alpha-2-adrenergic agonist, such as clonidine, and a growth hormone releasing peptide, such as GHRH, to restore or substantially enhance growth hormone release in such patients.

DETAILED DESCRIPTION OF THE INVENTION

While obese patients, and particularly obese children, have exhibited an impaired GH response which heretofore could not be restored with therapies shown to be effective in enhancing GH response in normal patients and short stature patients, a unique and effective treatment has now been found. This treatment involves administering cojointly to the obese patient an effective amount of an alpha-2-adrenergic agonist and a growth hormone releasing peptide.

The alpha-2-adrenergic agonist may be any of those which produce a post-synaptic stimulation of the alpha-2-adrenergic pathway so as to inhibit somatostatin release by the hypothalamus into the hypothalamic-pituitary portal system. Alpha-2-adrenergic agonists which may be utilized include clonidine (2-(2,6-dichloroanilino)-2-imidazoline), guanfacine, guanabenz, guanclofine, guanoxabenz (U.S. Pat. No. 4,910,215), and medetomidine (U.S. Pat. No. 4,910,214). Clonidine is preferred. The dosage is adjusted in accordance with the needs of the patient and the result desired. Typically, clonidine is administered orally at a dosage of about 100 to about 300 ug/m$^2$, preferably about 150 ug/m$^2$. It is preferably administered from 0 to about 120 minutes, most preferably about 60 minutes, prior to administering the growth hormone releasing peptide.

The growth hormone releasing peptide which may be utilized includes those peptides which stimulate a GH response at the GHRH level, i.e. stimulate the pituitary somatotropes. Such peptides include GHRH itself in its various known active forms such as GRF 1-44, GRF 1-40, GRF 1-37 and GRF 1-29. GHRH is typically administered by injection (i.v. or s.c.), and may be advantageously delivered in a pulsatile manner (e.g. by infusion pump). The dosage is typically about 1 ug/kg if administered by i.v. bolus, or about 10 ug/kg s.c.. Obviously, the dosage and frequency of administration can be adjusted to meet the needs of the particular patient under treatment and the desired objective.

Other growth hormone releasing peptides which can be effectively utilized are those short chain peptides (4–11 amino acids, preferably 5–7 amino acids) which have been recently found to stimulate a GH response similar to GHRH. These peptides include, but are not limited to those active peptides which are disclosed in U.S. Pat. Nos. 4,223,019, 4,223,020, 4,223,021, 4,224,316, 4,226,857, 4,228,155, 4,228,156, 4,228,157, 4,228,158, 4,410,512, 4,410,513, 4,411,890, 4,839,344, 4,880,777, 4,880,778, WO 89/07110, WO 89/07111 and WO 89/10933. Of the peptides disclosed in the above-identified patents, especially preferred are peptides of the formula:

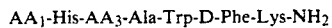

$AA_1$-His-$AA_3$-Ala-Trp-D-Phe-Lys-$NH_2$ wherein $AA_1$ is H or Ala and $AA_3$ is D-Trp or D-$\beta$-Nal, as well as analogs and derivatives thereof with similar activity.

EXAMPLE

Eight prepubertal obese children (boys), aged 10 to 12.4 years, all in good general health and taking no medication, participated in the study with informed consent (parent and child). All had height within normal percentiles for chronological age. Bone age was advanced 6–24 months in all but one patient and weight was above the 100th percentile for chronological age in all cases. The children were tested six times at random intervals ranging from 7 to 10 days, each patient serving as his own control. Studies commenced at 0900 h after an overnight fast and bed rest and thirty minutes after the insertion of a nontrombogenic catheter for blood withdrawal in a forearm vein. The study consisted of administering clonidine (Catapresan, Boehringer Ingelheim, Spain) orally at 150 micrograms/m$^2$ at time 0 followed by administering GHRH (GRF 1-29, Serono, Spain) as an intravenous bolus at 1 microgram/kg at time 60 minutes. The control experiments consisted of administering on separate occasions either clonidine at time 0 or GHRH at time 60 minutes. Blood samples for GH assays (RIA, BioMerieux, France) were taken at 15 minute intervals for two hours. The mean intra-assay coefficient of variation was 5.9, 4.6 and 3.9% at mean GH concentrations of 1.5, 8 and 24 micrograms/L respectively. To avoid inter-assay variations, all samples from a subject were run in the same assay.

Baseline plasma GH levels were not different in the 6 study days. Oral clonidine administration did not produce any significant plasma GH increase except for one patient who showed a maximal GH value of 6.5 ug/L at time 105 min. The mean amplitude of maximal GH plasma levels following clonidine challenge was 2.9±0.8 ug/L.

GHRH administration produced a slight but significant increase in plasma GH. The mean peak plasma GH level was 9.6±2 ug/L, a value significantly higher than after clonidine challenge, which peak appeared 45 minutes after administration. This GH response to GHRH in obese children is significantly less than the mean GH peak of 17.1±4.3 ug/L found in a control group of short children diagnosed as having constitutional growth delay. It is also significantly less than the reported GHRH-induced GH response in normal children and adolescents of 25.8±5.6 ug/L (9). This confirms previous reports of impaired GHRH-induced GH response in obese children.

Pretreatment with clonidine led to a clear and substantial GH response to GHRH with a peak value of 27.5±4.3 ug/L, significantly higher than any other study in obese children. Moreover, GH peaked earlier, 30 minutes after administering GHRH.

To confirm the uniqueness of the alpha-2-adrenergic agonist in achieving substantially enhanced GH response in obese patients versus another known GH potentiator which operates via a different mechanism (somatostatin inhibition via activation of cholinergic pathway), comparative experiments were performed with galanin (Bachem, Switzerland). Galanin (Gal) was administered alone, with clonidine (Clo) and with GHRH by infusion as a saline solution at 50 pmol/kg/min through a Millex-GY (0.22 um, Millipore) filter at time 55 to 120 minutes in all experiments. Also, for comparison purposes a similar group of short stature children diagnosed as having constitutional growth delay (CGD) were administered GHRH, galanin plus GHRH, and clonidine plus GHRH (previous study) by the same procedure.

The results of all the experiments are summarized in the following Table:

TABLE

| Patient Group | Therapy | Mean Peak GH Response (μg/L) |
|---|---|---|
| Obese | Clo | 2.9 ± 0.8 |
| | Gal | 4.1 ± 1.2 |
| | Clo + Gal | 5.8 ± 1.4 |
| | GHRH | 9.6 ± 2 |
| | Gal + GHRH | 12.6 ± 2.6 |
| | Clo + GHRH | 27.5 ± 4.3 |
| CGD | GHRH | 17.1 ± 4.3 |
| | Gal + GHRH | 31.6 ± 4.8 |
| | Clo + GHRH | 40.3 ± 3.9 (previous study) |

This data is evidence of dysfunction at the level of the central adrenergic pathways involved in GH neuroregulation. This dysfunction is responsible for the impaired GH secretion and the impaired GHRH-induced GH response in obese children and is consistent with the hypothesis that there is a chronic somatostatinergic hypertone in obesity. There also appears to be a GHRH defect in obese patients at the hypothalamic level. The combined treatment with clonidine and GHRH restored and enhanced growth hormone secretion in these patients well beyond any obesity therapy studied heretofore. Such therapy would considerably improve the therapeutic affect of a hypocaloric diet.

The superior effect of the alpha-2-adrenergic agonists such as clonidine is believed to result from the direct inhibition of somatostatin, unlike the indirect inhibition that occurs with the cholinergic agonists.

REFERENCE

1. Williams, N. Engl. J. Med. 311:1403, 1984
2. Kopelman, Clin. Endocrinol. 23:87, 1985
3. Kopelman, Clin. Endocrinol. 24:157, 1986
4. Loche, Clin. Endocrinol. 27:145, 1987
5. Cordido, J. Clin. Endocrinol. Metab., 68:290, 1989
6. Ghigo, J. Endocrinol Invest. 12:99, 1989
7. Davis, J. Clin. Endocrinol. Metab. 65:1248, 1987
8. Chatterjee, J. Endocrinol. 116:R1-R2, 1988
9. Reiter, J. Pediat. Endocrinol. 3:21, 1988
10. Arce, Neuroendocrinology 52/S1/90:119, 1990, Poster 3.50 of 2nd Int'l Cong. of Neuroendocrinology held Jun. 24–29, 1990
11. Ghigo, "Effects of the Enhancement of the Cholinergic Activity on Growth Hormone Secretion in Children: Clinical Implications", Recent Advances in Basic and Clinical Neuroendocrinology (eds. Casanueva and Dieguez) pp. 241–250, 1989, Excerpta Medica, Amsterdam

What is claimed is:

1. A method of inducing growth hormone secretion in an obese patient which comprises administering cojointly to said patient an effective amount of an alpha-2-adrenergic agonist and a growth hormone releasing peptide.
2. The method of claim 1 wherein said alpha-2-adrenergic agonist is clonidine.
3. The method of claim 2 wherein said clonidine is administered from 0 to about 120 minutes prior to said growth hormone releasing peptide.
4. The method of claim 3 wherein said growth hormone releasing peptide is GRF 1-44, GRF 1-40, GRF 1-37, or GRF 1-29.
5. The method of claim 2 wherein said clonidine is administered in an amount of about 100 to about 300 micrograms/m$^2$.
6. The method of claim 4 wherein said growth hormone releasing peptide is administered in an amount of about 1 ug/kg i.v. or about 10 ug/kg s.c..
7. The method of claim 4 wherein said clonidine is administered in an amount of about 150 micrograms/m$^2$.
8. The method of claim 1 wherein said growth hormone releasing peptide has the formula AA$_1$-His-AA$_3$-Ala-Trp-D-Phe-Lys-NH$_2$ wherein AA$_1$ is H or Ala and AA$_3$ is D-Trp or D-$\beta$-Nal.
9. A method of treating obesity which comprises administering to a patient with this condition an alpha-2-adrenergic agonist cojointly with a growth hormone releasing peptide in an amount effective to induce growth hormone secretion in said patient.
10. The method of claim 9 wherein said alpha-2-adrenergic agonist is clonidine.
11. The method of claim 10 wherein said clonidine is administered from 0 to about 120 minutes prior to said growth hormone releasing peptide.
12. The method of claim 11 wherein said growth hormone releasing peptide is GRF 1-44, GRF 1-40, GRF 1-37, or GRF 1-29.
13. The method of claim 10 wherein said clonidine is administered in an amount of about 100 to about 300 micrograms/m$^2$.

14. The method of claim 12 wherein said growth hormone releasing peptide is administered in an amount of about 1 ug/kg i.v. or about 10 ug/kg s.c..

15. The method of claim 12 wherein said clonidine is administered in an amount of about 150 micrograms/m$_2$.

16. The method of claim 9 which additionally comprises placing said patient on a hypocaloric diet.

17. The method of claim 9 wherein said growth hormone releasing peptide has the formula AA$_1$-His-AA$_3$-Ala-Trp-D-Phe-Lys-NH$_2$ wherein AA$_1$ is H or Ala and AA$_3$ is D-Trp or D-$\beta$-Nal.

* * * * *